United States Patent
Jeong et al.

(10) Patent No.: US 12,043,700 B2
(45) Date of Patent: Jul. 23, 2024

(54) POLYMER COMPOUND COMPRISING BIOMASS-DERIVED CYCLIC MONOMER AND PREPARATION METHOD THEREFOR

(71) Applicant: KOLON INDUSTRIES, INC., Seoul (KR)

(72) Inventors: Mee Hye Jeong, Seoul (KR); Ji Min Ha, Seoul (KR); Da Kyoung Yong, Seoul (KR); Ki Hyun Park, Seoul (KR)

(73) Assignee: KOLON INDUSTRIES, INC., Seoul (KR)

( * ) Notice: Subject to any disclaimer, the term of this patent is extended or adjusted under 35 U.S.C. 154(b) by 167 days.

(21) Appl. No.: 17/635,739

(22) PCT Filed: Aug. 28, 2020

(86) PCT No.: PCT/KR2020/011582
§ 371 (c)(1),
(2) Date: Feb. 16, 2022

(87) PCT Pub. No.: WO2021/040474
PCT Pub. Date: Mar. 4, 2021

(65) Prior Publication Data
US 2022/0356299 A1 Nov. 10, 2022

(30) Foreign Application Priority Data
Aug. 30, 2019 (KR) .................. 10-2019-0107106

(51) Int. Cl.
| | |
|---|---|
| *C08G 63/183* | (2006.01) |
| *B01J 23/46* | (2006.01) |
| *C07C 29/143* | (2006.01) |
| *C07C 45/59* | (2006.01) |
| *C08G 18/32* | (2006.01) |
| *C08G 18/76* | (2006.01) |
| *C08G 63/199* | (2006.01) |

(52) U.S. Cl.
CPC .......... *C08G 63/199* (2013.01); *B01J 23/462* (2013.01); *C07C 29/143* (2013.01); *C07C 45/59* (2013.01); *C08G 18/3212* (2013.01); *C08G 18/7671* (2013.01); *C08G 63/183* (2013.01)

(58) Field of Classification Search
CPC .......................... C08G 63/183; C08G 63/199
See application file for complete search history.

(56) References Cited

U.S. PATENT DOCUMENTS

| | | | |
|---|---|---|---|
| 8,927,675 B2 | 1/2015 | Rukavina | |
| 8,946,377 B2 | 2/2015 | Muelhaupt | |
| 9,822,211 B2 | 11/2017 | Rukavina | |
| 2009/0215933 A1* | 8/2009 | Kasai | C08G 63/199 |
| | | | 528/307 |
| 2010/0168372 A1 | 7/2010 | Berti | |
| 2016/0244556 A1* | 8/2016 | Kim | C08G 63/199 |
| 2018/0362807 A1 | 12/2018 | Choi | |

FOREIGN PATENT DOCUMENTS

| | | | |
|---|---|---|---|
| CN | 103159907 A * | 6/2013 | ............. B29C 48/08 |
| CN | 106866364 A | 6/2017 | |
| CN | 108620122 A | 10/2018 | |
| KR | 1020150047339 A | 5/2015 | |
| KR | 101558574 B1 | 10/2015 | |

OTHER PUBLICATIONS

CN-103159907-A_06-2013_English Translation.*
Noordzij, G. J., et al., "Small-scale screening of novel biobased monomers: the curious case of 1, 3-cyclopentanediol", RSC advances, 2018, 8, 70, pp. 39818-39828, S1-S36.
Li, G., et al., "Industrially scalable and cost-effective synthesis of 1, 3-cyclopentanediol with furfuryl alcohol from lignocellulose", Green Chemistry, 2016, 18, 12, pp. 3607-3613.
International Search Report dated Dec. 11, 2020.
The extended European Search Report dated Aug. 8, 2023.

* cited by examiner

*Primary Examiner* — Michael L Leonard
(74) *Attorney, Agent, or Firm* — Harvest IP Law, LLP (57) ABSTRACT

The present invention relates to a polyester or polyurethane polymer comprising a biomass-derived 1,3-cyclopentanediol monomer, and a method for preparing same.

5 Claims, 3 Drawing Sheets

POLYMER COMPOUND COMPRISING BIOMASS-DERIVED CYCLIC MONOMER AND PREPARATION METHOD THEREFOR

CROSS REFERENCE TO RELATED APPLICATIONS

This application is a National Stage of International Application No. PCT/KR2020/011582 filed Aug. 28, 2020, claiming priority based on Korean Patent Application No. 10-2019-0107106 filed Aug. 30, 2019

TECHNICAL FIELD

The present invention relates to a polymer compound including a biomass-derived 1,3-cyclopentanediol monomer and a method for preparing the same.

BACKGROUND ART

In general, polymers such as polycarbonate, polyester, and the like are prepared by using raw materials derived from petroleum resources. However, in recent years, as there is a concern about depletion of petroleum resources, polymer resins using raw materials obtained from biomass resources such as plants and the like are required. In addition, since there is also a concern about global warming due to an increase and accumulation of carbon dioxide emissions, which causes climate change, etc., development of polymers using plant-derived monomers that emit very little carbon during the manufacturing process as raw materials is required.

On the other hand, 1,3-cyclopentanediol is synthesized from cyclopentadiene, and the cyclopentadiene may be obtained by cracking dicyclopentadiene and reacted as shown in Reaction Scheme 1.

[Reaction Scheme 1]

The cyclopentadiene is highly reactive in the Diels-Alder reaction and converted back to the dicyclopentadiene within just a few hours at room temperature. Accordingly, the cyclopentadiene has a disadvantage of needing to be stored at −20° C. but used just for several days.

On the other hand, furfural is an organic compound derived from plants materials such as corn cobs, oats, bran, rice bran, bagasse, and sawdust. In other words, the furfural is a biomass-based chemical material, and the 1,3-cyclopentanediol may be prepared from the furfural.

On the other hand, conventional linear polyester has inferior transparency due to a low free volume of the entire polymer and is flexible due to the linearity but has a problem of soft strength, and conventional polyurethane has a problem of soft strength.

Accordingly, it is necessary to develop polyester having excellent transparency and strength and polyurethane having excellent strength is required, and in addition, to make the polyester and the polyurethane environmentally-friendly by using a biomass-derived monomer.

PRIOR ART

[Patent Document] Korean Patent Publication No. 10-1558574

DISCLOSURE

Technical Problem

In order to solve the above problems, the present inventors have conducted research and as a result, when biomass-derived 1,3-cyclopentanediol is included as a monomer of a polymer, an environmentally friendly polyester with excellent transparency and strength may be provided and polyurethane having excellent strength may be provided.

Accordingly, an object of the present invention is to provide an environmentally friendly polyester polymer having excellent transparency and strength, or an environmentally friendly polyurethane polymer having excellent strength, by including biomass-derived monomers.

Another object of the present invention is to provide a method for preparing a polyester polymer and a polyurethane polymer including a biomass-derived monomer.

Technical Solution

In order to achieve the above object, the present invention provides a polymer compound represented by Chemical Formula 1 including a 1,3-cyclopentanediol monomer:

[Chemical Formula 1]

wherein R is a compound of Chemical Formula 2 or Chemical Formula 3,

[Chemical Formula 2]

[Chemical Formula 3]

wherein * is a linking position,
a is an integer of 1 to 30, b is an integer of 1 to 30, and c is an integer of 1 to 30.

In addition, the present invention provides a polymer compound represented by Chemical Formula 4 including a 1,3-cyclopentanediol monomer:

wherein m is an integer of 1 to 30 and n is an integer of 1 to 30.

In addition, the present invention provides a method for preparing a polymer represented by Chemical Formula 1, which includes (i) adding a catalyst to an aqueous solution of furfuryl alcohol to prepare 4-hydroxy-2-cyclopentenone,
(ii) adding a catalyst to the 4-hydroxy-2-cyclopentenone to prepare 1,3-cyclopentanediol, and
(iii) mixing the 1,3-cyclopentanediol; terephthalic acid; and succinic anhydride or 2,5-furandicarboxylic acid to react them:

[Chemical Formula 1]

wherein R is a compound of Chemical Formula 2 or Chemical Formula 3,

[Chemical Formula 2]

[Chemical Formula 3]

wherein * is a linking position, and
a is an integer of 1 to 30, b is an integer of 1 to 30, and c is an integer of 1 to 30.

In addition, the present invention provides a method of preparing a polymer represented by Chemical Formula 4 which includes (i) adding a catalyst to a furfuryl alcohol aqueous solution to prepare 4-hydroxy-2-cyclopentenone;
(ii) adding a catalyst to the 4-hydroxy-2-cyclopentenone to prepare 1,3-cyclopentanediol; and
(iii) mixing the 1,3-cyclopentanediol and 4,4-diphenylmethane diisocyanate to react them.

[Chemical Formula 4]

wherein m is an integer of 1 to 30 and n is an integer of 1 to 30.

[Chemical Formula 4]

Advantageous Effects

The polyester polymer of the present invention is environmentally friendly including biomass-derived monomers, and thus it has excellent transparency due to an increase in a free volume of the polymer, and has excellent strength by including cyclic monomers.

In addition, the polyurethane polymer of the present invention is environmentally friendly by including biomass-derived monomers, and has an excellent strength effect.

MODE FOR INVENTION

Hereinafter, the present invention will be described in more detail.

Conventionally, 1,3-cyclopentanediol is prepared from cyclopentadiene derived from a non-renewable fossil fuel resource. However, materials produced from the fossil fuel resource, such as petroleum, have a limited reserve and need to be ungently replaced with environmentally-friendly materials due to high carbon dioxide emissions.

Accordingly, the present invention is to provide a polymer including a 1,3-cyclopentanediol monomer, which is prepared from a raw material extracted from biomass, wherein the polymer is not only environmentally-friendly and economical but also has excellent transparency due to the 1,3-cyclopentanediol monomer reducing crystallinity of the polymer and excellent strength due to a cyclic structure of the 1,3-cyclopentanediol monomer.

In other words, the present invention relates to a polymer compound represented by Chemical Formula 1 including the 1,3-cyclopentanediol monomer.

[Chemical Formula 1]

wherein R is a compound of Chemical Formula 2 or 3,

[Chemical Formula 2]

[Chemical Formula 3]

wherein * is a linking position,
a is an integer of 1 to 30, b is an integer of 1 to 30, and c is an integer of 1 to 30.

In addition, the present invention relates to a polymer compound represented by Chemical Formula 4 including a 1,3-cyclopentanediol monomer.

[Chemical Formula 4]

wherein m is an integer of 1 to 30 and n is an integer of 1 to 30.

The polymer compounds of Chemical Formula 1 and Chemical Formula 4 may include the 1,3-cyclopentanediol monomer, and the 1,3-cyclopentanediol may be a biomass-derived compound prepared from biomass-derived furfuryl alcohol.

Specifically, the biomass-derived 1,3-cyclopentanediol is prepared through a hydrogenation reaction of furfuryl alcohol, a derivative of furfural extracted from plant materials such as corn cobs, oats, bran, rice bran, and sawdust. Accordingly, a polymer of Chemical Formula 1 or Chemical Formula 4 including the biomass-derived 1,3-cyclopentanediol monomer may be environmentally-friendly and exhibit economical effects.

As R of the polymer compound of Chemical Formula 1 may have the compound of Chemical Formula 2, the polymer compound of Chemical Formula 1 may be a polymer compound of Chemical Formula 5.

[Chemical Formula 5]

The compound of Chemical Formula 2, succinic anhydride, may be bonded to the R position of Chemical Formula 1.

Therefore, the polymer compound of Chemical Formula 5 may be a random block copolymer of a 1,3-cyclopentanediol monomer, a terephthalic acid monomer, and a succinic anhydride monomer, which are biomass-derived compounds.

In addition, as R of the polymer compound of Chemical Formula 1 may have the compound of Chemical Formula 3, the polymer compound of Chemical Formula 1 may be a polymer compound of Chemical Formula 6.

[Chemical Formula 6]

2,5-furandicarboxylic acid as the compound of Chemical Formula 3 may be bonded to the R position of Chemical Formula 1.

Therefore, the polymer compound of Chemical Formula 6 may be a random block copolymer of a 1,3-cyclopentanediol monomer, a terephthalic acid monomer, and a 2,5-furandicarboxylic acid monomer, which are biomass-derived compounds.

When b of the polymer compound of Chemical Formula 1 is less than 1, transmittance and strength are low, but when the b is greater than 30, the cyclic structure (aromatic ring) of cyclopentane may increase birefringence, so that when the polymer compound of Chemical Formula 1 is formed into a film, image distortion may occur due to light scattering and viewing angles.

In addition, the molecular weight of the polymer compound of Chemical Formula 1 may be 10000 to 70000, and desirably 11700 to 55000.

When the molecular weight of the polymer compound of Chemical Formula 1 is less than 10000, the polymer compound becomes a polymer having a low molecular weight, deteriorating properties of the polymer such as tensile strength, flexural strength, and the like, but when the molecular weight is greater than 70000, as attraction between the polymers increases, the properties of the polymer such as tensile strength and flexural strength extremely increase, and when the polymer compound of Chemical Formula 1 is formed into a film, the film may be easily broken.

Conventional polyester not including the 1,3-cyclopentanediol monomer has a linear structure and thus a low free volume. Accordingly, excellent transparency is not secured. In addition, since a monomer with a cyclic structure is not included, excellent strength is not obtained.

However, the polymer compound of Chemical Formula 1 of the present invention includes the 1,3-cyclopentanediol monomer with a cyclic structure and thus has a three-dimensional structure, which increases a free volume and thereby increases fluidity of a polymer chain. Accordingly, excellent transparency may be obtained, and excellent strength also may be achieved due to the cyclic structure.

Specifically, the polymer compound of Chemical Formula 1 of the present invention has a transparency (haze) of 80% to 100%, desirably 85% to 100%, more desirably 95% to 100% of a 2 mm-thick specimen measured according to ASTM D1003. In addition, the flexural strength according to ASTM D-790 may be 120 N to 200 N, and the tensile strength according to ASTM D-638 may be 100 MPa to 200 MPa.

In addition, the polymer compound of Chemical Formula 4 may be a copolymer of a 1,3-cyclopentanediol monomer and 4,4-diphenylmethane diisocyanate, which are the biomass-derived compounds.

When n of the polymer compound of Chemical Formula 4 is less than 1, the polymer compound of Chemical Formula 4 becomes less hard and thus may lose rigidity, but when n is greater than 30, the polymer compound becomes extremely hard and thus may be easily broken.

In addition, the molecular weight of the polymer compound of Chemical Formula 4 may be 11000 to 60000, and desirably 11000 to 45000.

The conventional polyurethane that does not include the 1,3-cyclopentanediol monomer has a softness characteristic, but may have a rigid characteristic by including the 1,3-cyclopentanediol monomer.

Specifically, the polymer compound of Chemical Formula 4 of the present invention may have a flexural strength of 120 N to 200 N according to ASTM D-790 and a tensile strength of 110 MPa to 200 MPa according to ASTM D-638.

Therefore, the polymer compounds of Chemical Formula 1 and Chemical Formula 4, including the biomass-derived 1,3-cyclopentanediol monomer of the present invention, are environmentally friendly, and may have economical effects. In addition, the polymer compound of Chemical Formula 1 has excellent transparency and strength, and the polymer compound of Chemical Formula 4 has excellent strength.

In addition, the present invention relates to a method for preparing a polymer compound represented by Chemical Formula 1, which includes
(i) adding a catalyst to an aqueous solution of furfuryl alcohol to prepare 4-hydroxy-2-cyclopentenone,
(ii) adding a catalyst to the 4-hydroxy-2-cyclopentenone to prepare 1,3-cyclopentanediol, and
(iii) mixing the 1,3-cyclopentanediol; terephthalic acid; and succinic anhydride or 2,5-furandicarboxylic acid to react them:

[Chemical Formula 1]

wherein R is a compound of Chemical Formula 2 or Chemical Formula 3,

[Chemical Formula 2]

[Chemical Formula 3]

wherein * is a linking position, and
a is an integer of 1 to 30, b is an integer of 1 to 30, and c is an integer of 1 to 30.

The step (i) may be a process of adding a catalyst to an aqueous solution of furfuryl alcohol to prepare 4-hydroxy-2-cyclopentenone.

The furfuryl alcohol may be a derivative of furfural extracted from plant materials such as corn cobs, oats, bran, rice bran, and sawdust. In other words, the furfuryl alcohol may be a biomass-derived compound.

The step (i) uses water as a solvent, which is economical and environmentally friendly.

The catalyst of the step (i) may include at least one selected from calcium oxide, lead oxide, aluminum oxide, iron oxide, calcium chloride, zinc acetate, paratoluene sulfonic acid, stannous chloride, stannous sulfate, stannous oxide, tin oxide, stannous octoate, tetraphenyl tin, a tin powder, and titanium tetrachloride, and desirably calcium oxide.

The catalyst of the step (i) may be included in an amount of 0.1 to 10 wt %, and desirably 0.1 wt % to 5 wt % based on the total weight of the furfuryl alcohol aqueous solution. When the catalyst is included in an amount of less than 0.1 wt %, the reaction does not occur and 4-hydroxy-2-cyclopentenone may not be prepared, and when it exceeds 10 wt %, it is not economical because there are many unreacted catalysts.

In addition, in the step (i), 4-hydroxy-2-cyclopentenone may be prepared by stirring after adding a catalyst to a furfuryl alcohol aqueous solution, wherein stirring may be performed at a temperature of 100° C. to 300° C. for 10 minutes to 1 hour.

The step (ii) is adding a catalyst to the 4-hydroxy-2-cyclopentenone prepared in the step (i) to prepare 1,3-cyclopentanediol.

The catalyst is added to a solution in which the 4-hydroxy-2-cyclopentenone is dissolved in an organic solvent, wherein the organic solvent may include at least one selected from 2-methyltetrahydrofuran, methanol, and acetone, and desirably, 2-methyltetrahydrofuran.

In addition, the catalyst of the step (ii) may be a ruthenium-based catalyst. In the step (ii), 1,3-cyclopentanediol may be prepared by a hydrogenation reaction.

The catalyst of the step (ii) may be included in an amount of 0.1 wt % to 5 wt %, and desirably, 0.1 wt % to 3 wt % based on the total weight of the solution in which 4-hydroxy-2-cyclopentenone is dissolved in the organic solvent. When the catalyst is less than 0.1 wt %, the reaction does not occur, not obtaining 1,3-cyclopentanediol, but when included in an amount of greater than 5 wt %, it is not economical.

In addition, in the step (ii), the catalyst is added to the furfuryl alcohol aqueous solution and then stirred, preparing the 4-hydroxy-2-cyclopentenone, wherein the stirring may be performed under a hydrogen atmosphere at 70° C. to 200° C. for 2 hours to 6 hours.

The steps (i) and (ii) are shown in Reaction Scheme 2.

[Reaction Scheme 2]

The step (iii) is to mix and react the biomass-derived 1,3-cyclopentanediol prepared in the step (ii); terephthalic acid; and succinic anhydride or 2,5-furandicarboxylic acid; and in the step (iii), the polymer compound of Chemical Formula 1 is prepared.

Specifically, the step (iii) is to prepare the polymer compound of Chemical Formula 1 by adding the monomer to a tetrahydrofuran solvent under a nitrogen atmosphere and then stirring them at 150° C. to 250° C. for 2 hours to 6 hours.

In addition, the present invention provides a method of preparing a polymer represented by Chemical Formula 4 which includes:
(i) adding a catalyst to an aqueous solution of furfuryl alcohol to prepare 4-hydroxy-2-cyclopentenone;
(ii) adding a catalyst to the 4-hydroxy-2-cyclopentenone to prepare 1,3-cyclopentanediol; and
(iii) mixing the 1,3-cyclopentanediol and 4,4-diphenylmethane diisocyanate to react them:

wherein m is an integer of 1 to 30 and n is an integer of 1 to 30.

The steps (i) and (ii) are the same as the method for preparing the polymer compound of Chemical Formula 1.

The step (iii) is to mix and react the biomass-derived 1,3-cyclopentanediol prepared in the step (ii) and 4,4-diphenylmethane diisocyanate, preparing the polymer compound of Chemical Formula 4.

Specifically, the step (iii) is to add the monomer to a tetrahydrofuran solvent and then stirring them under a nitrogen atmosphere at 150° C. to 250° C. for 2 hours to 6 hours, preparing the polymer compound of Chemical Formula 1.

DETAILED DESCRIPTION OF THE EMBODIMENTS

Hereinafter, although described with reference to examples of the present invention, the following examples are for illustrating the present invention, and the scope of the present invention is not limited thereto.

Preparation Example 1. Preparation of Poly(CPdiol-co-TPA)

An aqueous solution was prepared by dissolving 14 g of furfuryl alcohol, a derivative of furfural extracted from biomass, in 685.97 mL of water. Subsequently, 0.028 g of calcium oxide was added to the aqueous solution and then stirred at 200° C. for 0.5 hours, preparing 4-hydroxy-2-cyclopentenone.

Then, 248 g of the 4-hydroxy-2-cyclopentenone was dissolved in 2000 mL of 2-methyltetrahydrofuran, preparing a solution. 4 g of ruthenium was added to the solution to perform a hydrogenation reaction at 120° C. for 4 hours, preparing biomass-derived 1,3-cyclopentanediol.

50 g of the 1,3-cyclopentanediol (Cpdiol) and 20 g of terephthalic acid (TPA) were added to tetrahydrofuran and then stirred under a nitrogen atmosphere at 200° C. for 4 hours, preparing a polymer compound represented by Chemical Formula 7 and having a molecular weight of 12000 g/mol.

[Chemical Formula 7]

Comparative Preparation Example 1. Preparation of Poly(EG-co-TPA)

50 g of ethylene glycol (EG) and 50 g of terephthalic acid (TPA) were added to tetrahydrofuran and then stirred under a nitrogen atmosphere at 200° C. for 4 hours, preparing a

[Chemical Formula 4]

polymer compound represented by Chemical Formula 8 and having a molecular weight of 40000 g/mol.

[Chemical Formula 8]

Experimental Example 1. Measurement of Molecular Structure of Polyester

The polymer of Chemical Formula 7 according to Preparation Example 1 and the polymer of Chemical Formula 8 according to Comparative Preparation Example 1 were measured with respect to a bending degree by using the Gaussian 09 program.

Figure 1:
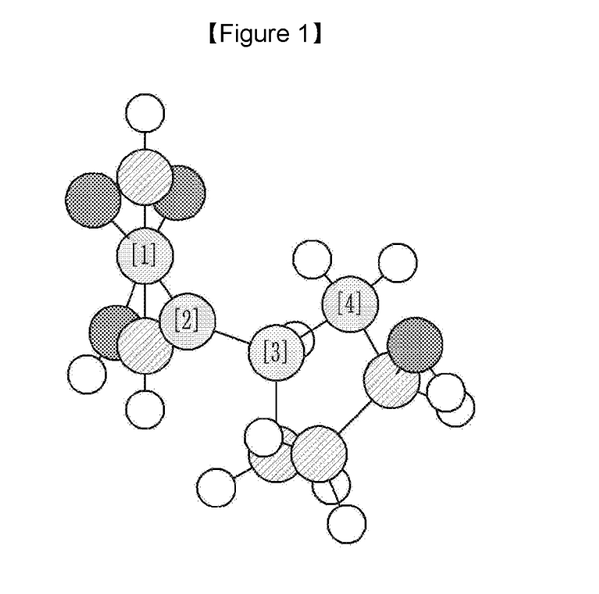
FIG. 1 is a three-dimensional structural diagram showing a degree of bending of Chemical Formula 7.
Figure 2:
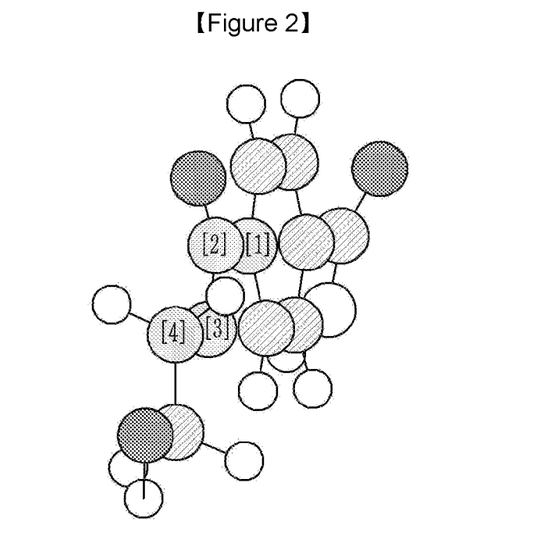
FIG. 2 is a three-dimensional structural diagram showing a degree of bending of Chemical Formula 8.
Figure 3:
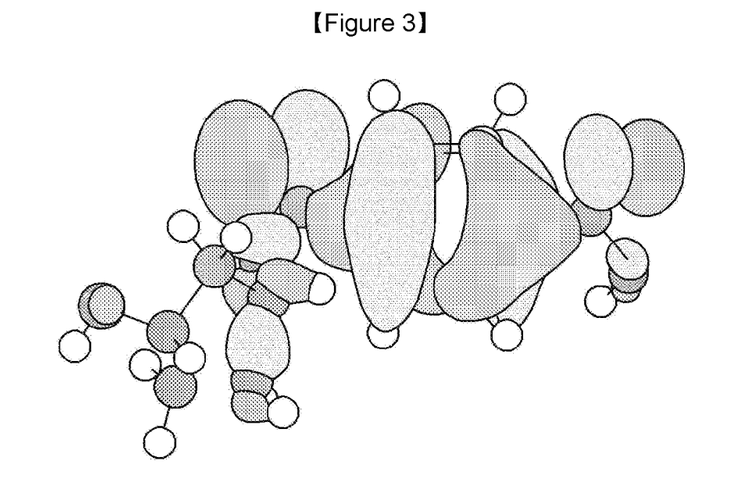
FIG. 3 is a HOMO electron cloud distribution diagram of a three-dimensional structural formula of Chemical Formula 7.
Figure 4:
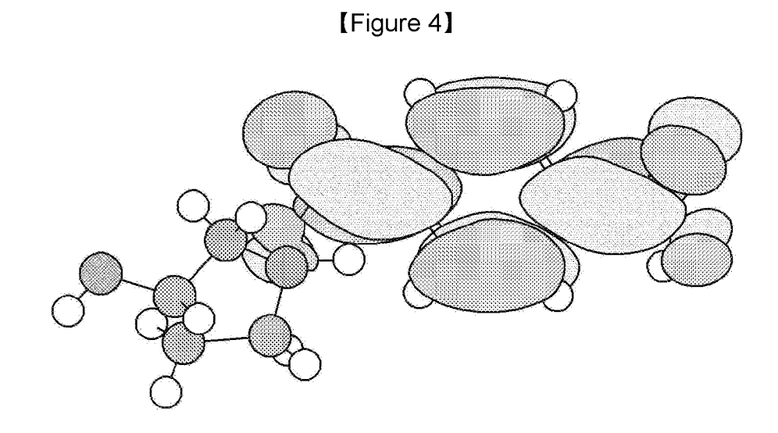
FIG. 4 is a LUMO electron cloud distribution diagram of a three-dimensional structural formula of Chemical Formula 7.
Figure 5:
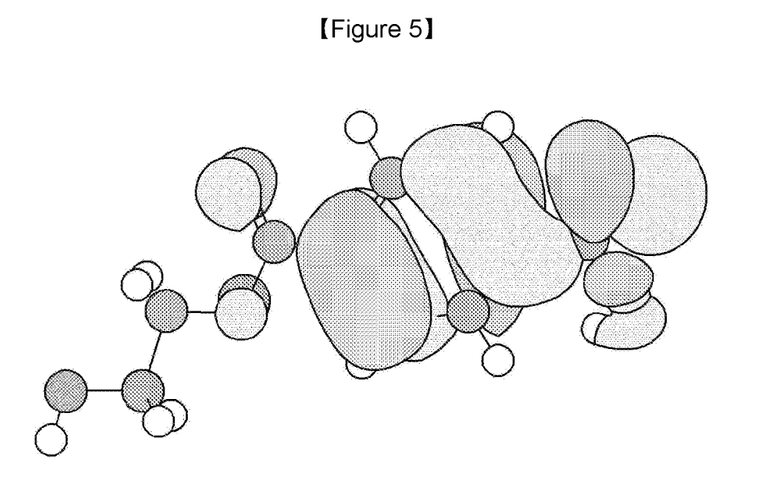
FIG. 5 is a HOMO electron cloud distribution diagram of a three-dimensional structural formula of Chemical Formula 8.
Figure 6:
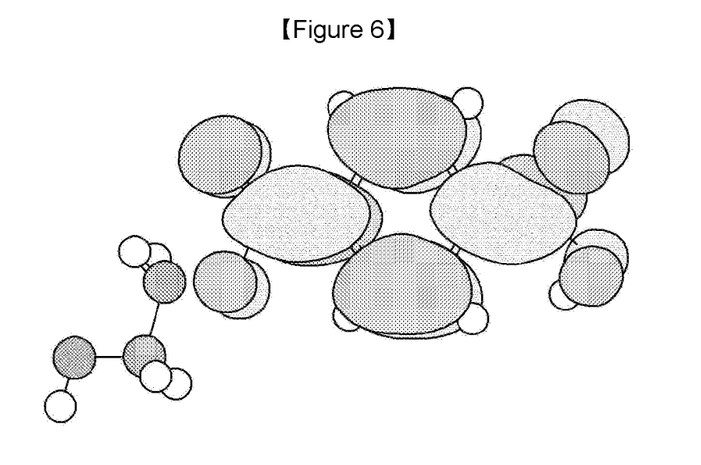
FIG. 6 is a LUMO electron cloud distribution diagram of a three-dimensional structural formula of Chemical Formula 8.

As a result, the polymer of Chemical Formula 7 including a biomass-derived 1,3-cyclopentanediol monomer had a bending degree of 101.59° (FIG. 1), and the polymer of Chemical Formula 8 including no 1,3-cyclopentanediol monomer had a bending degree of 179.99°, which showed a linear structure (FIG. 2).

In other words, when the biomass-derived 1,3-cyclopentanediol monomer was included, the polymer had a three-dimensional structure, and when polymerized thereby, the polymer was expected to have a higher free volume.

In addition, electron distribution diagrams of the polymer of Chemical Formula 7 according to Preparation Example 1 and the polymer of Chemical Formula 8 according to Comparative Preparation Example 1 are shown in FIGS. 3 to 6, and HOMO and LUMO energy levels of the polymers of Chemical Formulas 7 and 8 are shown in Table 1.

TABLE 1

|  | Chemical Formula 7 | Chemical Formula 8 |
| --- | --- | --- |
| HOMO (eV) | −7.31 | −7.44 |
| LUMO (eV) | −2.07 | −2.13 |

Referring to the results of Table 1, the polymer of Chemical Formula 7 including the biomass-derived 1,3-cyclopentanediol monomer exhibited higher HOMO and LUMO energy levels than the polymer of Chemical Formula 8 including no 1,3-cyclopentanediol monomer. This result exhibits that the polymer including the biomass-derived 1,3-cyclopentanediol monomer had excellent thermal stability and high transmittance (transparency), compared with the polymer including no biomass-derived 1,3-cyclopentanediol monomer.

Example 1. Preparation of Poly[3-methoxy-3-oxo-propanoyloxy]cyclopentyl methyl terephthalate 1,3-cyclopentanediol was prepared in the same manner as in Preparation Example 1.

50 g of the 1,3-cyclopentanediol, 20 g of terephthalic acid, and 30 g of succinic anhydride were added to tetrahydrofuran and then stirred under a nitrogen atmosphere at 200° C. for 4 hours, preparing a polymer represented by Chemical Formula 5 and having a molecular weight of 30084.48 g/mol.

[Chemical Formula 5]

Example 2. Preparation of Poly[5-(4-methoxybutoxy)carbonyl]furan-2-carboxylic 4-(methyoxycarbonyl)benzoic anhydride]

1,3-cyclopentanediol was prepared in the same manner as in Preparation Example 1.

50 g of the 1,3-cyclopentanediol, 20 g of terephthalic acid, and 30 g of 2,5-furandicarboxylic acid (FDCA) were added to tetrahydrofuran and then stirred under a nitrogen atmosphere at 200° C. for 4 hours, preparing a polymer represented by Chemical Formula 6 and having a molecular weight of about 50000 g/mol.

[Chemical Formula 6]

Example 3. Preparation of Poly[3-methoxycyclopentyl-4-(4-acetamidobenzyl)phenylcarbamate]

1,3-cyclopentanediol was prepared in the same manner as in Preparation Example 1.

50 g of the 1,3-cyclopentanediol and 50 g of 4,4-diphenylmethane diisocyanate were added to tetrahydrofuran and then stirred under a nitrogen atmosphere at 200° C. for 4 hours, preparing a polymer represented by Chemical Formula 4 and having a molecular weight of about 40000 g/mol.

[Chemical Formula 4]

Comparative Example 1. Preparation of Polyester 20 g of terephthalic acid, 30 g of 2,5-furandicarboxylic acid, and 50 g of butylene glycol were added to tetrahydrofuran and then stirred under a nitrogen atmosphere at 200° C. for 4 hours, preparing a polymer represented by Chemical Formula 9 and having a molecular weight of about 20000 g/mol.

[Chemical Formula 9]

Comparative Example 2. Preparation of Polyurethane 20 g of 4,4-diphenylmethane diisocyanate and 20 g of ethylene glycol were added to tetrahydrofuran and then stirred under a nitrogen atmosphere at 230° C. for 4 hours, preparing a polymer represented by Chemical Formula 10 and having a molecular weight of about 50000 g/mol.

[Chemical Formula 10]

Experimental Example 2. Measurement of Physical Properties of Polymer Compounds The polymer compound represented by Chemical Formula 5 according to Example 1, the polymer compound represented by Chemical Formula 5 according to Example 2, the polymer compound represented by Chemical Formula 4 according to Example 3, the polymer compound represented by Chemical Formula 9 according to Comparative Example 1, and the polymer compound represented by Chemical Formula 10 according to Comparative Example 2 were measured with respect to transparency, flexural strength, and tensile strength, and the results are shown in Table 2.

The transparency, the flexural strength, and the tensile strength are measured as follows.

Transparency (transmittance): measured according to ASTM D1003. According to ASTM D1003, 2.0 mm-thick specimens were measured with respect to light transmittance (total light transmittance) by using a hazemeter (NDH 5000W, Nippon Denshoku Industries Co., Ltd.).

Flexural strength: measured according to ASTM D-790. According to ASTM D-790, flexural strength specimens were prepared and measured with respect to flexural strength at 23±2° C. under RH of 50±5% after 24 hours by using a universal testing machine (UTM). Herein, a cross-head speed of the universal testing machine was set to 5 mm/min.

Tensile strength: measured according to ASTM D-638. According to ASTM D-638, a tensile strength specimen was prepared and measured with respect to tensile strength at room temperature by using the universal testing machine (UTM). Herein, the cross-head speed of the universal testing machine (UTM) was set to 5 mm/min.

TABLE 2

|  | Transparency (%) | Flexural strength (N) | Tensile strength (MPa) |
| --- | --- | --- | --- |
| Example 1 | 97.2 | 170 | 150 |
| Example 2 | 98.2 | 150 | 120 |
| Example 3 | 98.4 | 155 | 130 |
| Comparative Example 1 | 80.3 | 100 | 98 |
| Comparative Example 2 | 81.2 | 98 | 100 |

As a result, the polymer compounds of Chemical Formulas 5 and 6 including a monomer of biomass-derived 1,3-cyclopentanediol according to the present invention exhibited more excellent transparency than that of the polymer according to Chemical Formula 9.

The transparency was related to a measurement result of a molecular structure, and the polymer compounds of Chemical Formulas 5 and 6 included 1,3-cyclopentanediol and thus had a three-dimensional structure, which increased a free volume and thus fluidity of a polymer chain, and accordingly, exhibited excellent transparency.

On the other hand, the polymer compound of Chemical Formula 9 had a linear structure and exhibited no increase in a free volume and thus had insufficient transparency, compared with the polymer compounds of Chemical Formulas 5 and 6.

In addition, the polymer compounds of Chemical Formulas 4, 5, and 6 including biomass-derived 1,3-cyclopentanediol as a monomer according to the present invention exhibited excellent flexural strength and tensile strength, compared with the polymer compounds of Chemical Formulas 9 and 10.

The reason is that since strength was obtained by 1,3-cyclopentanediol with a cyclic structure included as a monomer, a polymer compound of the present invention including the biomass-derived 1,3-cyclopentanediol as a monomer exhibited excellent flexural strength and tensile strength.

INDUSTRIAL APPLICABILITY

The present invention relates to a polymer compound including a biomass-derived 1,3-cyclopentanediol monomer and a method of manufacturing the same, and the polyester polymer of the present invention includes the biomass-derived monomer and thus is environmentally-friendly, exhibits excellent transparency due to an increase in a free volume, and in addition, includes a cyclic monomer and thus exhibits excellent strength.

While this invention has been described in connection with what is presently considered to be practical example embodiments, it is to be understood that the invention is not limited to the disclosed embodiments. On the contrary, it is intended to cover various modifications and equivalent arrangements included within the spirit and scope of the appended claims.

The invention claimed is:

1. A polymer compound represented by Chemical Formula 1 comprising a biomass-derived 1,3-cyclopentanediol monomer:

[Chemical Formula 1]

wherein R is a compound of Chemical Formula 2 or Chemical Formula 3,

[Chemical Formula 2]

[Chemical Formula 3]

wherein * is a linking position, and
a is an integer of 1 to 30, b is an integer of 1 to 30, and c is an integer of 1 to 30.

2. The polymer compound of claim 1, wherein the 1,3-cyclopentanediol included in Chemical Formula 1 is a compound prepared from a biomass-derived furfuryl alcohol.

3. The polymer compound of claim 1, wherein the polymer compound of Chemical Formula 1 is a random copolymer of a 1,3-cyclopentanediol monomer, a terephthalic acid monomer, and a succinic anhydride monomer, or
a random copolymer of a 1,3-cyclopentanediol monomer, a terephthalic acid monomer, and a 2,5-furandicarboxylic acid monomer.

4. The polymer compound of claim 1, wherein the polymer compound of Chemical Formula 1 has a molecular weight of 10000 to 70000.

5. The polymer compound of claim 1, wherein the polymer compound of Chemical Formula 1 has transparency of 80% to 100% according to ASTM D1003, a flexural strength of 120 N to 200 N according to ASTM D-790, and a tensile strength of 100 MPa to 200 MPa according to ASTM D-638.

* * * * *